(12) United States Patent
Nakai et al.

(10) Patent No.: US 6,534,477 B2
(45) Date of Patent: Mar. 18, 2003

(54) PRODUCTION AND USE OF MODIFIED CYSTATINS

(75) Inventors: Shuryo Nakai, Vancouver (CA); Masahiro Ogawa, Vancouver (CA); Soichiro Nakamura, Matsue (JP)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/775,932

(22) Filed: Feb. 2, 2001

(65) Prior Publication Data

US 2002/0137671 A1 Sep. 26, 2002

Related U.S. Application Data

(63) Continuation of application No. PCT/CA99/00717, filed on Aug. 5, 1999
(60) Provisional application No. 60/095,503, filed on Aug. 5, 1998.

(51) Int. Cl.[7] .................. C12N 15/15; C12N 15/03; A61K 38/55; C07K 14/00
(52) U.S. Cl. ............... 514/8; 514/2; 514/12; 514/21; 514/25; 514/42; 530/395; 530/350; 536/23.1; 536/24.3; 435/69.1; 435/320.1; 435/325; 435/252.3; 435/471
(58) Field of Search ............... 530/350, 395; 514/2, 8, 12, 25, 21, 42; 536/23.1, 24.3; 435/69.1, 320.1, 325, 252.3, 471

(56) References Cited

U.S. PATENT DOCUMENTS

| | | | |
|---|---|---|---|
| 4,902,509 A | 2/1990 | Turk et al. ............... | 514/2 |
| 5,432,264 A | 7/1995 | Grubb et al. ............. | 530/350 |

FOREIGN PATENT DOCUMENTS

| | | | | |
|---|---|---|---|---|
| JP | 01-124389 | 5/1989 | | |
| JP | 01-202287 | 8/1989 | | |
| WO | WO 88/09384 | * 12/1988 | ........... | C12P/21/02 |
| WO | WO 96/16173 | 5/1996 | | |

OTHER PUBLICATIONS

Abrahamson M. et al. (1988) *FEBS Letters* 236 (1): 14–18.
Barrett AJ. et al. Methods Enzymol. (1981) 80:771–778.
Barrett AJ. et al. The Biochemical Journal (1986) *Letters* 236 (1):312.
Barrett AJ. (1987) *TIBS 12*: 193–196.
Ekiel I. et al. J Mol. Biol. (1997) 271(2):266–77.
Li F. et al. Comparative Biochemistry and Physiology. Part B, Biochemistry and Molecular Biology (1998) 121(2):135–43.
Nakamura S. et al., Journal of Biological Chemistry (1993) 268(17):12706–12712.
Nakamura S. et al., FEBS Letters (1993) 328(3):259–262.
Nakamura S. et al. FEBS Letters (1996) 383:251–254.
Nakamura S. et al., Abstract for poster presented at the Canadian Institute of Food Science and Technology annual conference (dated Aug. 18, 1996).
Nakamura S. et al., Journal of Agricultural and Food Chemistry (1998) 46(7):2882–2887.
Nakamura S. et al., FEBS Letters (1998) 427(2):252–254.
NI J. et al., Journal of Biological Chemistry (1997) 272(16):10853–10858.
Tsai YJ. et al. Comparative Biochemistry and Physiology. Part B, Biochemistry and Molecular Biology (1996) 113(3):573–580.
Turk V. et al. (1991) *FEBS* 285(2): 213–219.
Urwin PE. et al. Plant Journal (1995) 8(1):121–131.
Yamashita M. et al. Journal of Biochemistry (1996) 120(3):483–487.
International Search Report WO 00/08159.

* cited by examiner

*Primary Examiner*—Karen Cochrane Carlson
*Assistant Examiner*—Chih-Min Kam
(74) *Attorney, Agent, or Firm*—Klarquist & Sparkman, LLP

(57) ABSTRACT

Cystatins that have been modified by glycosylation in order to enhance stability and activity are disclosed, as are methods of making such cystatins and methods of using such cystatins to inhibit proteolysis.

4 Claims, 6 Drawing Sheets

```
              10                    20
S S P G K P P R L V G G P M D A S V E E E G V 30                    40
R R A L D F A V G E Y N K A S N D M Y H S R A
                  N S
                    T 50                   60
L Q V V R A R K Q I V A G V N Y F L D V E L G 70                 80                   90
R T T C T K T Q P N L D N C P F H D Q P H L K
                    S
                    T 100                 110
R K A F C S F Q I Y A V P W Q G T M T L S K S

120
T C Q D A
```

Fig. 1: Human cystatin C

```
                  10                    20
S S S K E E N R I I P G G I Y D A D L N D E W V 30                    40
Q R A L H F A I S E Y N K A T E D E Y Y R R P L
          N               N S
                            T 50                   60                   70
Q V L R A R E Q T F G G V N Y F F D V E V G R T 80                   90
I C T K S Q P N L D T C A F H E Q P E L Q K K Q
                  N T
                    S 100                 110                 120
L C S F E I Y E V P W E D R M S L V N S R C Q E A
```

Fig. 2: Human cystatin S

```
              10                    20
W S P K E E D R I I P G G I Y N A D L N D E W V
              30                    40
Q R A L H F A I S E Y N K A T K D D Y R R P L
            N           N S
                          T
        50                    60                    70
R V L R A R Q Q T V G G V N Y F F D V E V G R T
              80                    90
I C T K S Q P N L D T C A F H E Q P E L Q K K Q
              N S
                T
        100                   110                   120
L C S F E I Y E V P W E N R R S L V K S R C Q E S
```

Fig. 3: Human cystatin SN

```
              10                    20
W S P Q E E D R I I E G G I Y D A D L N D E R V
              30                    40
Q R A L H F V I S E Y N K A T E D E Y Y R R L L
            N           N S
                          T
        50                    60                    70
R V L R A R E Q I V G G V N Y F F D I E V G R T
              80                    90
I C T K S Q P N L D T C A F H E Q P E L Q K K Q
              N S
                T
        100                   110                   120
L C S F Q I Y E V P W E D R M S L V N S R C Q E A
```

Fig. 4: Human cystatin SA

```
                  10                        20
G S A S A Q S R T L A G G I H A T D L N D K S V 30                        40
Q C A L D F A I S E Y N K V I N K D E Y Y S R P
            N             S       S   N
                          T       T 50                   60                        70
L Q V M A A Y Q Q I V G G V N Y Y F N V K F G R T 80                  90
T C T K S Q P N L D N C P F N D Q P K L K E E E
                  S   S       S
                  T   T       T 100                 110                     120
F C S F Q I N E V P W E D K I S I L N Y K C P K V
```

Fig.5: Human cystatin D

```
                  10                        20
L P R D A R A R P Q E R M V G E L R D L S P D 30                        40
D P Q V Q K A A Q A A V A S Y N M G S N S I Y
                  N             N S N     S
                                  T       T 50                   60
Y F R D T H I I K A Q S Q L V A G I K Y F L T 70                        80                  90
M E M G S T D C R K T R V T G D H V D L T T C
              N       N             N N 100                 120
P L A A G A Q Q E K L R C D F E V L V V P W Q

130
N S S Q L L K H N C V Q M
```

Fig.6: Human cystatin M

```
                    10                              20
        R P Q E R M V G E L R D L S P D D P Q V Q K A 30                              40
        A Q A A V A S Y N M G S N S I Y Y F R D T H I
                    N         N S N     S
                              T         T 50                       60
        I K A Q S Q L V A G I K Y F L T M E M G S T D 70                       80                       90
        C R K T R V T G D H V D L T T C P L A A G A Q
                              N N 100                             110
        Q E K L R C D F E V L V V P W Q N S S Q L L K

120
        H N C V Q M
```

Fig.7: Human cystatin E

```
                         10                              20
        S E D R S R L L G A P V P B D E N D E G L Q R 30                              40
        A L Q F A M A E Y N R A S N D K Y S S R V V R
                         N S         S N
                         T           T
                                     N 50                       60
        V I S A K R Q L V S G I K Y I L Q V E I G R T 70                       80                       90
        T C P K S S G D L Q S C E F H D E P E M A K Y
                    N                                N N 100                             110
        T T C T F V V Y S I P W L N Q I K L L E S K C Q
```

Fig.8: Egg White cystatin

```
                    10                      20
      Q G P R K G R L L G G L M E A D V N E E G V Q 30                      40
      E A L S F A V S E F N K R S N D A Y Q S R V V
                  N         N S         S N
                            T           T 50                      60
      R V V R A R K Q V V S G M N Y F L D V E L G R 70                   80                      90
      T T C T K S Q A N L D S C P F H N Q P H L K R
                        N S                 S
                        T                   T 100                     110
      E K L C S F Q V Y V V P W M N T I N L V K F S

C Q D
```

Fig.9: Bovine cystatin

```
                    10                      20
      T G I P G G L V D A D I N D K D V Q K A L R F 30                      40
      A V D H Y N G Q S N D A F V R K V S K V I K V
                  N S         S           N
                  T           T 50                      60
      Q Q Q V A A G M K Y I F T V K M E V A S C K K 70                   80                      90
      G G V K T M C A V P K N P S I E Q V I Q C K I
                                                  N 100                     110
      T V W S Q P W L N S L K V T E N T C M
```

Fig.10: Carp cystatin

```
              10                    20
G L I G G P M D A N M N D Q G T R D A L Q F A 30                40
V E H N K K T N D M F V R Q V A K V V N A Q K
      N S         S
      T           T 50                60                70
Q V V S G M K Y I F T V Q M G R T P C R K G G 80                90
V E K V C S V H K D P Q M A V P Y K C T F E V
                                  N 100               110
W S R P W M S D I Q M V K N Q C E S
```

Fig.11: Trout cystatin

```
              10                    20
G L V G G P M D A N M N D Q G T R D A L Q F A 30                40
V V E H N K K T N D M P V R Q V A K V V N A Q
        N S         S
        T           T 50                60
K Q V V S G M K Y I F T V Q M G R T P C R K G 70                80                90
G V E K I C S V H K D P Q M A V P Y K C T F E
                                    N 100               110
V W S R P W M S D I Q M V K N Q C E S
```

Fig.12: Chum salmon cystatin

PRODUCTION AND USE OF MODIFIED CYSTATINS

CROSS-REFERENCE TO RELATED APPLICATIONS

This is a continuation of International Application No. PCT/CA99/00717, filed Aug. 5, 1999, which claims the benefit of U.S. Provisional Application No. 60/095,503, filed Aug. 5, 1998, both of which are herein incorporated by reference.

FIELD OF THE INVENTION

The present invention relates to protease inhibitors, specifically to cystatins, that have been modified by glycosylation in order to enhance stability and activity; to methods of making such modified protease inhibitors and to methods of using such modified protease inhibitors to inhibit proteolysis of a protein substrate.

BACKGROUND

Proteases are enzymes that degrade proteins. Proteases are classified by the substrate upon which they act and include serine proteases, cysteine proteases, aspartate proteases and metalloproteinases. Serine and cysteine proteases are widespread and are found in diverse organisms including eukaryotic and prokaryotic animals and plants. Cysteine proteases are generally well characterized enzymes having a known primary structure composed of alpha helices and beta pleated sheets (8).

Proteases mediate many processes that are harmful to man, either by producing pathology or by causing economic loss, for instance by degrading foods. Protease-mediated pathology is known to be caused by a wide variety of organisms including bacteria, such as staphylococci and streptococci, fungi, arthropods, nematodes, protozoa such as amoebas, intestinal flagellates, haemoflagelates, such as Leishmania and trypanosomes and helminths.

Proteases are known to be important in the pathology of certain viruses (9, 11, 12, 31) including Polio virus, Herpes virus, Corona virus, HIV and Rotavirus. Proteases are also known to play a role in various diseases with no clear etiological agent, such as muscular dystrophy (7) and cancers (1) including breast cancer (2), and amyloid angiopathy, a genetic disease that often leads to fatal cerebral hemorrhages in young adults (10, 13).

Proteases are also responsible for the spoilage of economically important foodstuffs, necessitating huge annual expenditures on preventative measures. For instance, the fungus *Botrytis cinera* causes widespread disease in over thirty species of commercial crop plants. Molds and fungi are the major destroyers of citrus fruit crops. Foods rich in protein, such as meat and fish, are degraded and made inedible by proteases from Pseudomonads and other bacteria. Foods with a high muscle content may be quickly broken down by endogenous proteases released from tissues upon death. These enzymes degrade myosin, and destroy the texture of the food. An important example of such spoilage occurs during the processing of surimi, which is a form of processed minced fish, commonly made from Pacific Whiting (*Merluccius productus*), and is the main ingredient of seafood analogs such as "imitation crab meat". Surimi is an important source of relatively cheap, high quality, low fat protein important to the diet of many people in the Far East and of increasing economic significance worldwide. Endogenous proteolytic enzymes released during surimi production cause rapid degradation of muscle tissue and lead to poor quality surimi (3, 4, 5, 6, 11, 17, 18, 19). It is thought that the protease released from the fish tissue is a cathepsin, which is a common cysteine protease (3).

Because of the role of proteases in these various processes, protease inhibitors have been investigated for their potential role in preventing disease and degradation of foodstuffs (4, 5, 18). Partially refined substances that contain protease inhibitors are commonly used in food processing, for instance, to prevent proteolytic breakdown of fish protein during the production of surimi (4, 17, 18). The most commonly used food-grade protease inhibitors are beef plasma protein (BPP), egg white powder and potato powder (4). Genetic engineering techniques have been used to introduce protease-inhibitor genes from chickens into cereal and grass plants to control protease-producing plant pathogens. Likewise, a plant protease inhibitor gene, from Cowpea, has been recombinantly introduced into tobacco, tomato, cotton and other plants to inhibit destruction by nematode worms (16).

Cystatins are cysteine protease inhibitors that are members of Family 2 of the cystatin superfamily, characterized by a single chain of about 115 to 122 amino acids with a molecular weight of about 13000, having two disulfide bonds (7, 8, 10). Cystatins and protease enzymes such as cathepsins form tight (but reversible) enzyme-inhibitor complexes with dissociation constants typically in the nannomolar range (10).

A number of cystatins have been characterized including human cystatins (C, S, SN, SA, D, M and E), mouse cystatin, egg-white cystatin, bovine cystatin, carp cystatin, trout cystatin and salmon cystatin. In their natural state, cystatins protect the body by inhibiting the potentially harmful effects of proteolysis, and may prevent destruction of connective tissue by protease enzymes, for instance, lysosomal proteases, released from dying or damaged cells (16).

Cystatins have been investigated for potential medical applications, for instance, to inhibit replication and pathology of Picornaviruses (12), Coronaviruses (9) and Herpes Simplex type 1 virus (15, 16, 30). Cystatins may also play a natural role in prevention of bacterial infection by *E. coli*, Shigella (13), Leishmania, Schistosoma and Entamobea (10) which appear to use proteases to facilitate tissue invasion.

Cystatins are likely the primary protease inhibitors in food-grade protease inhibitor preparations such as beef plasma protein and egg white powder. Since cystatins are themselves proteins, they are prone to denaturation and loss of activity when exposed to unfavorable temperatures or pH. Many food production processes, including surimi production, involve elevated temperatures (17). Presently, in order to maintain cystatin activity, more cystatin must be added after cooling. Adding additional cystatin is both labor-intensive and expensive. Also, when cystatins are used for medical treatment, either as a topical or ingested medication, it is preferable for the cystatin-containing composition to be sterile. A common method of sterilization involves treatment with elevated temperatures. A cystatin that could maintain activity despite exposure to elevated temperatures would thus be useful in food processing and in drug formulation.

SUMMARY OF THE DISCLOSURE

The present invention provides modified, glycosylated, heat-stable cystatins and methods of making and using these cystatins. The present invention also provides nucleic acid molecules encoding such cystatins.

The nucleic acid molecules of the invention have been modified so that when such a nucleic acid molecule is expressed in a eukaryotic cell, certain amino-acid residues of the expressed cystatin protein are glycosylated during post-translational modification of the protein. The resulting mature protein has attached, at specific amino acid residues, sugar molecule chains of varying length. The present invention includes the nucleic acid molecules that encode modified cystatins based on the cystatins from humans (C, S, SN, SA, D, M and E), egg white, cow, carp, trout and salmon.

Various residues in the cystatin primary amino acid sequence have been identified where the introduction glycosylated residues increases heat stability of the expressed protein without severely affecting enzymatic activity. In human cystatin C, for instance, the sites for glycosylation include amino acid residues at positions 35, 36 and 79.

The present invention also includes a method of making modified heat-stable cystatins by modifying the nucleic acid molecules that encode cystatins. Such nucleic acid molecules are modified at certain defined sites and expressed in a eukaryotic cells. The present invention also includes a cell that contains at least one nucleic acid molecule encoding at least one modified, glycosylated, heat-stable cystatin. The cells of the invention may be of many types, for instance they may be cells from a yeast, a mammal, an insect, or a plant.

The invention also includes methods of inhibiting proteolysis of a protein substrate by contacting the protein substrate with a modified heat-stable cystatin having at least one engineered glycosylation site. Such a method may be applied, for example, to food processing, such as the production of surimi.

The invention also includes a method of treating a protease-mediated pathology of an organism, such as a mammal, a fish or a plant by administering to the organism a modified heat-stable cystatin of the invention. By such administration, the modified heat-stable cystatin contacts the protease that mediates the pathology, thereby inhibiting proteolysis by the protease and thereby treating the pathology.

SEQUENCE LISTING

SEQ ID NO: 1 shows the cDNA sequence and the amino acid sequence of native human cystatin C.

SEQ ID NO: 2 shows the amino acid sequence of native human cystatin C.

SEQ ID NO: 3 shows the cDNA sequence and the amino acid sequence of native human cystatin S.

SEQ ID NO: 4 shows the amino acid sequence of native human cystatin S.

SEQ ID NO: 5 shows the cDNA sequence and the amino acid sequence of native human cystatin SN.

SEQ ID NO: 6 shows the amino acid sequence of native human cystatin SN.

SEQ ID NO: 7 shows the cDNA sequence and the amino acid sequence of native human cystatin SA.

SEQ ID NO: 8 shows the amino acid sequence of native human cystatin SA.

SEQ ID NO: 9 shows the cDNA sequence and the amino acid sequence of native human cystatin D.

SEQ ID NO: 10 shows the amino acid sequence of native human cystatin D.

SEQ ID NO: 11 shows the cDNA sequence and the amino acid sequence of native human cystatin M.

SEQ ID NO: 12 shows the amino acid sequence of native human cystatin M.

SEQ ID NO: 13 shows the cDNA sequence and the amino acid sequence of native human cystatin E.

SEQ ID NO: 14 shows the amino acid sequence of native human cystatin E.

SEQ ID NO: 15 shows the cDNA sequence and the amino acid sequence of native egg white cystatin.

SEQ ID NO: 16 shows the amino acid sequence of native egg white cystatin.

SEQ ID NO: 17 shows the cDNA sequence and the amino acid sequence of native carp cystatin.

SEQ ID NO: 18 shows the amino acid sequence of native carp cystatin.

SEQ ID NO: 19 shows the cDNA sequence and the amino acid sequence of native salmon cystatin.

SEQ ID NO: 20 shows the amino acid sequence of native salmon cystatin.

SEQ ID NO: 21 shows the cDNA sequence and the amino acid sequence of native trout cystatin.

SEQ ID NO: 22 shows the amino acid sequence of native trout cystatin.

SEQ ID NO: 23 shows the cDNA sequence and the amino acid sequence of native bovine cystatin.

SEQ ID NO: 24 shows the amino acid sequence of native bovine cystatin.

SEQ ID NO: 25 shows the first of four oligonucleotides used to create a nucleotide coding for modified human cystatin C.

SEQ ID NO: 26 shows the second of four oligonucleotides used to create a nucleotide coding for synthetic human cystatin C.

SEQ ID NO: 27 shows the third of four oligonucleotides used to create a nucleotide coding for synthetic human cystatin C.

SEQ ID NO: 28 shows the fourth of four oligonucleotides used to create a nucleotide coding for synthetic human cystatin C.

SEQ ID NO: 29 shows a forward primer used in site-directed mutagenesis to introduce a glycosylation site at residue 35 of a modified human cystatin C.

SEQ ID NO: 30 is a reverse primer used in site-directed mutagenesis to introduce a glycosylation site at residue 35 of a modified human cystatin C.

SEQ ID NO: 31 is the forward primer used in site-directed mutagenesis to introduce a glycosylation site at residue 36 of a modified human cystatin C.

SEQ ID NO: 32 is the reverse primer used in site-directed mutagenesis to introduce a glycosylation site at residue 36 of a modified human cystatin C.

BRIEF DESCRIPTION OF THE DRAWINGS

FIG. 1 shows the native amino acid sequence of the mature human cystatin C peptide without its signal sequence. Amino acid modifications for introducing glycosylation sites are shown below the native sequence.

FIG. 2 shows the native amino acid sequence of the mature human cystatin S peptide without its signal sequence. Amino acid modifications for introducing glycosylation sites are shown below the native sequence.

FIG. 3 shows the native amino acid sequence of the mature human cystatin SN peptide without its signal sequence. Amino acid modifications for introducing glycosylation sites are shown below the native sequence.

FIG. 4 shows the native amino acid sequence of the mature human cystatin SA peptide without its signal sequence. Amino acid modifications for introducing glycosylation sites are shown below the native sequence.

FIG. 5 shows the native amino acid sequence of the mature human cystatin D peptide without its signal sequence. Amino acid modifications for introducing glycosylation sites are shown below the native sequence.

FIG. 6 shows the native amino acid sequence of the mature human cystatin M peptide without its signal sequence. Amino acid modifications for introducing glycosylation sites are shown below the native sequence.

FIG. 7 shows the native amino acid sequence of the mature human cystatin E peptide without its signal sequence. Amino acid modifications for introducing glycosylation sites are shown below the native sequence.

FIG. 8 shows the native amino acid sequence of the mature Egg White cystatin peptide without its signal sequence. Amino acid modifications for introducing glycosylation sites are shown below the native sequence.

FIG. 9 shows the native amino acid sequence of the mature bovine cystatin without its signal sequence. Amino acid modifications for introducing glycosylation sites are shown below the native sequence.

FIG. 10 shows the native amino acid sequence of the mature carp cystatin without its signal sequence. Amino acid modifications for introducing glycosylation sites are shown below the native sequence.

FIG. 11 shows the native amino acid sequence of the mature trout cystatin without its signal sequence. Amino acid modifications for introducing glycosylation sites are shown below the native sequence.

FIG. 12 shows the native amino acid sequence of the mature chum salmon cystatin without its signal sequence. Amino acid modifications for introducing glycosylation sites are shown below the native sequence.

DESCRIPTION OF THE INVENTION

A. Definitions

A protein is said to be modified when it has been intentionally, artificially altered from its naturally occurring, wild-type form, e.g., when the primary amino acid sequence of a cystatin protein has been intentionally, artificially altered to add a non-native glycosylation site somewhere in the protein. A DNA sequence is said to be modified when it has been intentionally, artificially altered from its naturally occurring, wild-type form, e.g., when the nucleotide coding for a cystatin protein has been mutated by site-directed mutagenesis to create a non-native nucleotide addition, deletion of substitution. The term engineered may be used synonymously with the term modified.

To say that an organism, or nucleotide sequence has been genetically engineered means that it has been intentionally, artificially genetically altered from its naturally occurring, wild-type genetic form, for instance, a DNA sequence is said to be genetically engineered when its sequence has been intentionally, artificially genetically altered from its wild-type sequence. Any genetically engineered organism or nucleotide sequence has been modified.

Heat stability refers to the ability of a protein to function at high temperatures. Proteins typically lose activity as the temperature is raised above their normal in vivo operating range, and generally become denatured as the temperature increases further. A modified protein may be more heat stable than the unmodified form of the protein, meaning that the modified form of the protein retains greater activity at higher temperatures than the unmodified form of the protein.

To say a feature has been introduced means that a non-wild-type feature has been intentionally, artificially added, for instance, a glycosylation site may be said to be introduced into a protein if it has been intentionally, artificially added to the protein, also a nucleotide may be said to be introduced into a cell or other nucleotide sequence when it has been intentionally, artificially added into a cell or sequence, likewise, a deletion may be introduced into a DNA sequence. Likewise, amino acid substitutions, additions and deletions may be introduced into a protein.

A glycosylation site is a place on a molecule at which sugars may be added. The addition of sugars (glycosylation) may occur at introduced sites in modified proteins such as at amino acid residue 37 of the modified human cystatin C.

A glycosylation site in a protein is denoted by the general formula X (#) Z, where X=the native amino acid that has been removed, and #=the position of that amino acid in the protein, and Z=the substituted amino acid that has been inserted in place of X. For instance, Ala (37) Ser denotes that Alanine at position 37 has been removed and replaced with Serine; likewise, for one-letter code, A (31) N denotes that Alanine at position 31 has been removed and replaced with Asparagine. The numbering system of cystatin proteins in this text reflects that shown in the accompanying figures. While alternative numbering systems are possible, the nomenclature use herein is intended to identify a particular amino acid residue, rather than any residue that happens to be at a given distance from an arbitrary point on an amino acid sequence.

An organism refers to any organism of any kingdom, phylum, class, order, family, genus or species.

A pathology refers to a state that is measurably or detectably at variance with normal, healthy, non-disease-state physiology.

A cancer refers to any neoplastic transformation or any tissue that has undergone neoplasia and includes solid, non-solid, benign and malignant transformed tissue of both plants and animals.

A protease-mediated pathology is any pathology that is caused in part or in whole by the action of a protease, for instance, the proteolytic invasion of human tissue by a cancer cell, the proteolytic destruction of human tissue by a bacterium or a protozoan (e.g., Pseudomonas or Leishmania) and the tissue destruction of a plant by a fungus (e.g., *Phytopthora infestans*) are all examples of protease-mediated pathologies.

To say that a polynucleotide (or a gene or genome) is recombinant means that it has been altered by the addition at some site of non-native nucleic acids or nucleotides, i.e., nucleotides that are not normally found in the particular polynucleotide, or that are not normally found at that site. For instance, a human cystatin gene that has been altered by nucleotide substitution is said to be recombinant. Likewise, a recombinant protein is a protein that is the product of a recombinant polynucleotide and that contains non-native amino acid residues.

An isolated nucleic acid has been substantially separated or purified away from other nucleic acid sequences in the cell of the organism in which the nucleic acid naturally occurs, i.e., other chromosomal and extrachromosomal DNA and RNA. The term isolated thus encompasses nucleic acids purified by standard nucleic acid purification methods. The term also embraces nucleic acids prepared by recombinant expression in a host cell as well as chemically synthesized nucleic acids.

Nucleic acid probes and primers may readily be prepared based on the nucleic acid sequences provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are well known in the field of molecular biology. Primers are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art. Probes and primers as used in the present invention preferably comprise at least 15 nucleotides of the nucleic acid sequences that encode a modified cystatin protein. In order to enhance specificity, longer probes and primers may also be employed, such as probes and primers that comprise 20, 30 or 40 consecutive nucleotides of the disclosed nucleic acid sequences. Methods for preparing and using probes and primers are described in a number of reference works, for example Sambrook et al. (1989) (26); Ausubel et al., (1987) (25); Innis et al., (1990) (27). PCR primer pairs can be derived from a known sequence, for example, by using computer programs intended for that purpose such as Primer (Version 0.5, 1991, Whitehead Institute for Biomedical Research, Cambridge, Mass.).

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term purified peptide does not require absolute purity, rather, it is intended as a relative term. Thus, for example, a purified cystatin preparation is one in which cystatin is enriched compared to the cystatin in its natural environment, i.e., within a cell. A purified preparation of a cystatin is prepared such that the cystatin represents at least 20% of the portion of the protein content of the preparation. Preparations comprising at least 50%, 75% or at least 90% cystatin (expressed as a percentage of total protein) may be desirable for certain applications.

B. General Methods

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al., (1989)(25) and Ausubel et al., (1987)(26).

(1) Production, cloning and expression of modified cystatins

A modified nucleotide sequence that codes for a cystatin protein having at least one glycosylation site may be produced by making synthetic sequences using a commercial polynucleotide synthesizer. The synthetic nucleotides are designed on the basis of the known nucleotide sequence of the cystatin gene and the known codon usage for the cell type in which the nucleotides are to be expressed. A suitable target site for the introduction of a glycosylation site is identified based on the primary amino acid sequence of the cystatin to be modified. A nucleotide sequence is designed that will code for a peptide that includes such a site. The synthetic nucleotide sequence may then be synthesized as described herein. A series of anti-parallel and complementary nucleotides may be synthesized and annealed together to form synthetic double-stranded nucleotide fragment. These fragments may then be ligated together to produce a contiguous double-stranded nucleotide that codes for a particular cystatin having one or more engineered glycosylation sites. The synthetic nucleotides may be amplified in vitro using the Polymerase Chain Reaction (PCR) (27) so that many copies of the nucleotide are available for cloning into a prokaryotic cloning vector (26) or into an expression vector, as explained below.

Additional glycosylation sites may be introduced using site-directed mutagenesis to add, delete or substitute particular amino acid residues. Various standard techniques are known to carry out site-directed mutagenesis (26, chapter 15), and commercial kits are also available such as the QUICKCHANGE™ mutagenesis site-directed mutagenesis kit (STRATAGENE™, CA). Nucleotides may be modified or synthesized so as to include restriction enzyme sites that can be used for cloning.

The modified nucleotide may be cloned into a standard prokaryotic cloning vector, for example pBR322, pUC18 or pUC19 (26, chapter 1). The sequence of the cloned nucleotide may be checked by sequencing using standard methods (26, chapters 1 and 13).

Modified nucleotides may be cloned into an expression vector that allows protein production in a particular cell type. Since the proteins of the invention are glycosylated, it is required that the cell type in which the proteins are expressed can readily carry out post-translational modification including glycosylation. Typically, a eukaryotic cell is used that glycosylates peptides at the Asn-X-Ser/Thr motif. Yeast cells are commonly used for such a purpose. Standard cloning techniques may be used (26, chapter 9). Such expression vector/cell systems are well known and commercially available and include vector/cell combinations that carry out post-translational modifications required for the proper expression of glycosylated eukaryotic proteins. Various yeast strains and yeast-derived vectors are commonly used for this type of expression, for instance, Pichia pastoris expression systems that may be used to practice the present invention may be obtained from INVITROGEN™. Such systems include suitable Pichia pastoris strains, vectors, reagents, transformants, sequencing primers and media. Available strains include a GS115 his 4 deficient strain, a KM71 aox1 deficient strain, a GS115 His$^+$ Mut$^-$ strain for extracellular expression and a His$^+$ Mut$^-$ strain for intracellular expression (33).

Non-yeast eukaryotic vectors may equally be used for expression of the modified nucleotides. Mammalian vector / host cell systems that contain genetic and cellular control elements capable of carrying out transcription, translation and post-translational modification are well known in the art. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines, which are available from INVITROGEN™.

The cloned expression vector may then be transformed into a particular cell type and the nucleotide expressed. Many different types of cell may be used to express the modified nucleic acid molecules. Examples of such cells include cells of yeasts, fungi, insects and humans and plants, including transformed and non-transformed cells. For instance, common mammalian cells that could be used for the invention include human HeLa cells, SW-527 human cells (ATCC deposit #7940), WISH cells (ATCC deposit #CCL-25), Daudi cells (ATCC deposit #CCL-213), Mandin-Darby bovine kidney cells (ATCC deposit #CCL-22) and Chinese Hamster ovary cells (ATCC deposit #CRL-2092). Common yeast cells include Pichia pastoris (ATCC deposit #201178) and *Saccharomyces cerevisiae* (ATCC deposit #46024). Insect cells include cells from *Drosophila melanogaster* (ATCC deposit #CRL-10191), the cotton bollworm (ATCC deposit #CRL-9281) and from *Trichoplusia ni* egg cell homoflagelates. Fish cells that may be used include those from rainbow trout (ATCC deposit #CLL-55), salmon (ATCC deposit #CRL-1681) and Zebrafish (ATCC deposit #CRL-2147). Amphibian cells that may be used include those of the Bullfrog, *Rana catesbelana* (ATCC deposit #CLL-41). Reptile cells that may be used include those from Russell's Viper (ATCC deposit #CCL-140). Plant cells that could be used include Chlamydomonas cells (ATCC deposit #30485), Arabidopsis cells (ATCC deposit #54069) and tomato plant cells (ATCC deposit #54003). Many of these cell types are commonly used and are available from the ATCC as well as from commercial suppliers such as PHARMACIA™ and INVITROGEN™.

Expressed protein may be accumulated within a cell or may be secreted from the cell. Such expressed protein may then be collected and purified. This protein may then be characterized for activity and heat stability and may be used to practice the methods of the invention.

The amino acid sequences of the cystatins (FIGS. 1–12) are shown in their mature form without a signal peptide. The signal peptide is cleaved off during post-translational modification to produce the mature peptide. The invention may be equally practiced with cystatin peptides which retain the signal peptide.

(2) Measurement of protease activity and heat resistance

Protease inhibition activity of modified cystatins is assayed by measuring the reduction in activity of the protease papain. A substrate is used that releases nitroaniline into the reaction medium. The amount of nitroaniline released is determined by measuring light absorption by the solution. This assay is described in detail in Example 4, below.

Heat resistance of the modified cystatin is determined by heating a solution containing a known amount of modified cystatin, cooling it, and adding it to a mixture containing a known amount of protease and a known amount of protein. Protease activity is measured by determining turbidity of the mixture after a set time and also by using the nitroaniline assay as described below.

(3) Methods of using modified cystatins

The modified cystatins of the invention may be used to inhibit proteolysis of a protein substrate in generally the same way as non-modified cystatins are used. Such uses include inhibition of proteolysis in food processing (4), therapeutic treatment of viral disease such as those caused by Herpes Simplex (11, 30), picornaviruses (20) and coronavirus (9).

The present invention includes a general method of inhibiting proteolysis of a substrate by providing the modified cystatin and by contacting this cystatin with the substrate. Such a substrate may be any substrate containing protein. Such a modified cystatin may be used in food processing applications, in agricultural applications and in human and non-human medical applications. For instance, a protein substrate such as minced Pacific Whiting (as used for surimi production) may be treated with a modified cystatin of the invention to inhibit proteolysis caused by the release of endogenous protease from the fish tissue. Suggested concentrations for the application of modified cystatin are, for instance, for surimi processing, from about 1 $\mu$g/g to 100 $\mu$g/g of surimi.

The present invention also includes methods of using a modified cystatin for the inhibition of proteases for therapeutic purposes. For instance, the cystatins of the invention may be used to inhibit tissue destruction and invasion by pathogens such as staphylococci and streptococci. Streptococcus is the etiological agent of the common skin disease impetigo, and certain particularly rapacious "flesh eating" strains of Staphylococcus and Streptococcus have recently received much media attention, particularly because of their multiple antibiotic resistance.

The effectiveness of cystatins of the invention in preventing bacterial invasion of host-tissues can be measured, for example, by the method of Betts and Finlay (32). This method can be used to determine tissue invasion of green monkey kidney cells (ATCC deposit #CCL-70) by bacteria such as *E. coli* and *Salmonella typhimurium*.

For medical applications the modified cystatin may be administered topically or systemically. The cystatin may be formulated with a carrier or pharmacologically acceptable excipient. For instance, the cystatin may be mixed with a carrier such as a petroleum-based or lanolin-based oil to form a gel, and administered topically at the site of infection, thereby contacting the modified cystatin with the protease and preventing tissue destruction.

The cystatins of the present invention may also be administered systemically, either orally, intravenously, subcutaneously, transdermally or by other methods. For instance, the cystatin of the present invention may be formulated into a tablet or solution form and administered orally. Formulation of drugs into pills and tablets is well known in the art. Systemic administration may be used to treat infections that cannot be treated topically such as cancer and systemic viral infections of humans and animals.

For topical medical treatment, concentrations of modified cystatin in a cream or ointment may be from about 1 ng to 100 mg per gram total weight of ointment, or may be from about 1 $\mu$g to 1 mg total weight, or may be from about 10 $\mu$g to 100 $\mu$g total weight. For ingested medications, the amount of modified cystatin per Kg mass of a patient may be from about 1 ng to 100 mg, or may be from about 1 $\mu$g to 1 mg, or may be from about 10 $\mu$g to 100 $\mu$g.

The cystatins of the present invention may be used to inhibit proteolysis caused by pathogens of crop plants and fruits. For instance, the modified cystatins may be applied to the surface of fruit or crops to inhibit proteases produced by plant pathogens such as fungi, for instance, Botrytis. The modified cystatin may, for instance, be sprayed or painted onto crops, either in a pure form or diluted in a carrier liquid such as water.

The cystatins of the invention show superior heat resistance, maintaining a high degree of activity after exposure to elevated temperatures. These heat resistant cystatins may be particularly useful where sterility is required, such as in medical applications where it is generally desirable for medicines to be uncontaminated with biological organisms. For instance, the cystatins of the present invention may be formulated into topical ointments or pills which may then be packaged and sterilized and administrated therapeutically. Also, food processing, such as surimi production, involves elevated temperatures. The cystatins of the invention are useful in such processes due to their enhanced resistance.

C. Production of Modified Human Cystatin C

Glycosylation of one or more amino acid residues at specific sites in the human cystatin C peptide increases heat stability of the cystatin without substantially inhibiting functionality. Glycosylation at other, inappropriate sites, may drastically decrease or destroy the protein's inhibitory function. The invention identifies three amino acid residues of human cystatin C that may be modified to introduce a glycosylation site; one or more of these sites may be modified to produce a cystatin protein having superior properties, such as enhanced heat stability.

The amino acid sequences for native and modified human cystatin C are shown in FIG. 1. Amino acid substitutions to produce glycosylation sites are shown directly beneath the amino acids of the native protein. One or more of these amino acid substitutions may be present in a modified cystatin protein of the present invention. The cDNA sequence for native human cystatin C is shown in SEQ ID NO: 1.

Human cystatin C protein may be modified to introduce glycosylation sites (Asn-X-Ser/Thr) at amino acid residues 35, 36 or 79 by the introduction of amino acid substitutions at positions 37, 36 or 81, respectively. One or more of the following specific substitutions may be made: Ala (37) Ser, Ala (37) Thr, Lys (36) Asn, Asp (81) Ser, Asp (81) Thr.

It should be noted that the peptide of cystatin C in FIG. 1 is shown in its mature form without a signal peptide. The signal peptide is cleaved off during post-translational modification to produce the mature peptide. The invention may be equally practiced with cystatin peptides which retain the signal peptide.

The same is so for all the other cystatins, FIGS. 2–12.

D. Production of Modified Human Cystatin S

The amino acid sequences for native and modified human cystatin S are shown in FIG. 2. Amino acid substitutions to introduce glycosylation sites are shown directly beneath the amino acids of the native protein. One or more such amino acid substitutions may be present in the protein of the present invention. The cDNA sequence for native human cystatin S is shown in SEQ ID NO: 3.

The human cystatin S protein may be modified by the introduction of the following amino acid substitutions: Ala (31) Asn, Lys (37) Asn, Ala (38) Ser, Ala (38) Thr, Leu (81) Asn, Asp (82) Thr, and Asp (82) Ser.

E. Production of Modified Human Cystatin SN

The amino acid sequences for native and modified human cystatin SN are shown in FIG. 3. Amino acid substitutions to introduce glycosylation sites are shown directly beneath the amino acids of the native protein. One or more such amino acid substitutions may be present in the protein of the present invention. The cDNA sequence for native human cystatin SN is shown in SEQ ID NO: 5.

The human cystatin SN protein may be modified to introduce one or more glycosylation sites by the introduction of one or more of the following amino acid substitutions: Ala (31) Asn, Ala (38) Ser, Ala (38) Thr, Lys (37) Asn, Lys (81) Asn, Asp (82) Ser, Asp (82) Thr.

F. Production of Modified Human Cystatin SA

The amino acid sequences for native and modified human cystatin SA are shown in FIG. 4. Amino acid substitutions to introduce glycosylation sites are shown directly beneath the amino acids of the native protein. One or more such amino acid substitutions may be present in the protein of the present invention. The cDNA sequence for native human cystatin SA is shown in SEQ ID NO: 7.

The human cystatin SA protein may be modified by the introduction of the following amino acid substitutions: Val (31) Asn, Ala (38) Ser, Ala (38) Thr, Lys (37) Asn, Asp (82) Ser, Asp (82) Thr, Leu (81) Asn.

G. Production of Modified Human Cystatin D

The amino acid sequences for native and modified human cystatin D are shown in FIG. 5. Amino acid substitutions to introduce glycosylation sites are shown directly beneath the amino acids of the native protein. One or more such amino acid substitutions may be present in the protein of the present invention. The cDNA sequence for native human cystatin D is shown in SEQ ID NO: 9.

The human cystatin D protein may be modified by the introduction of the following amino acid substitutions: Ala (31) Asn, Val (38) Ser, Val (38) Thr, Asp (42) Ser, Asp (42) Thr, Asp (83) Ser, Asp (83) Thr, Pro (86) Ser, Pro (86) Thr, Gln (90) Ser, Gln (90) Thr, Tyr (44) Asn.

H. Production of Modified Human Cystatin M

The amino acid sequences for native and modified human cystatin M are shown in FIG. 6. Amino acid substitutions to introduce glycosylation sites are shown directly beneath the amino acids of the native protein. One or more such amino acid substitutions may be present in the protein of the present invention. The cDNA sequence for native human cystatin M is shown in SEQ ID NO: 11.

The human cystatin M protein may be modified by the introduction of the following amino acid substitutions: Val (35) Asn, Met (40) Asn, Gly (41) Ser, Gly (41) Thr, Ser (42) Asn, Ile (45) Ser, Ile (45) Thr, Arg (78) Asn, Arg (81) Asn, Asp (88) Asn, Leu (89) Asn.

I. Production of Modified Human Cystatin E

The amino acid sequences for native and modified human cystatin E are shown in FIG. 7. Amino acid substitutions to introduce glycosylation sites are shown directly beneath the amino acids of the native protein. One or more such amino acid substitutions may be present in the protein of the present invention. The cDNA sequence for native human cystatin E is shown in SEQ ID NO: 13.

The human cystatin E protein may be modified by the introduction of the following amino acid substitutions: Val (28) Asn, Met (33) Asn, Gly (34) Ser, Gly (34) Thr, Ser (35) Asn, Ile (38) Ser, Ile (38) Thr, Asp (81) Asn, Leu (82) Asn.

J. Production of Modified Egg White Cystatin

The amino acid sequences for native and modified egg white cystatin are shown in FIG. 8. Amino acid substitutions to introduce glycosylation sites are shown directly beneath the amino acids of the native protein. One or more such amino acid substitutions may be present in the protein of the present invention. The cDNA sequence for native egg white cystatin is shown in SEQ ID NO: 15.

The egg white cystatin protein may be modified by the introduction of the following amino acid substitutions: Ala (35) Ser, Ala (35) Thr, Arg (34) Asn, Lys (39) Ser, Lys (39) Thr, Lys (39) Asn, Tyr (40) Asn, Leu (78) Asn, Lys (91) Asn, Tyr (92) Asn.

K. Production of Modified Bovine Cystatin

The amino acid sequences for native and modified bovine cystatin are shown in FIG. 9. Amino acid substitutions to introduce glycosylation sites are shown directly beneath the amino acids of the native protein. One or more such amino acid substitutions may be present in the protein of the present invention. The cDNA sequence for native bovine cystatin is shown in SEQ ID NO: 23.

The bovine cystatin protein may be modified by the introduction of the following amino acid substitutions: Ala (29) Asn, Arg (36) Ser, Arg (36) Thr, Lys (35) Asn, Ala (40) Ser, Ala (40) Thr, Tyr (41) Asn, Leu (79) Asn, Asp (80) Ser, Asp (80) Thr, Pro (88) Ser, Pro (88) Thr.

L. Production of Modified Carp Cystatin

The amino acid sequences for native and modified carp cystatin are shown in FIG. 10. Amino acid substitutions to introduce glycosylation sites are shown directly beneath the amino acids of the native protein. One or more such amino acid substitutions may be present in the protein of the present invention. The cDNA sequence for native carp cystatin is shown in SEQ ID NO: 17.

The carp cystatin protein may be modified by the introduction of the following amino acid substitutions: Gln (31) Ser, Gln (31) Thr, Gly (30) Asn, Ala (35) Ser, Ala (35) Thr, Lys (39) Asn, Lys (91) Asn.

M. Production of Modified Trout Cystatin

The amino acid sequences for native and modified trout cystatin are shown in FIG. 11. Amino acid substitutions to introduce glycosylation sites are shown directly beneath the amino acids of the native protein. One or more such amino acid substitutions may be present in the protein of the present invention. The cDNA sequence for native trout cystatin is shown in SEQ ID NO: 21.

The trout cystatin protein was modified by the introduction of the following amino acid substitutions: Lys (29) Asn, Lys (30) Ser, Lys (30) Thr, Met (34) Thr, Met (34) Ser, Lys (39) Asn, Lys (88) Asn.

N. Production of Modified Chum Salmon Cystatin

The amino acid sequences for native and modified chum salmon cystatin are shown in FIG. 12. Amino acid substitutions to introduce glycosylation sites are shown directly beneath the amino acids of the native protein. One or more such amino acid substitutions may be present in the protein of the present invention. The CDNA sequence for native chum salmon cystatin is shown in SEQ ID NO: 19.

The chum salmon cystatin protein may be modified by the introduction of the following amino acid substitutions: Lys (29) Asn, Lys (30) Ser, Lys (30) Thr, Met (34) Ser, Met (34) Thr, Lys (88) Asn.

EXAMPLE 1

Synthesis of Nucleotide Sequences that Code for Modified Human Cystatin C

Cloning was done using the pUC19 cloning vector and *E. coli* using standard gene cloning techniques (26). The yeast strain *Pichia pastons* KM71 was used to express mammalian genes and constructs. T4 DNA ligase, restriction enzymes, the 7-DEAZA sequencing kit and blunting kit were all purchased from TAKARA SHUZO™ of Kyoto, Japan. The oligonucleotide in vitro mutagenesis system (version 2) was purchased from AMERSHAM™ International. CM TOYO-PEARL™ 650M resin was purchased from TOSOH™ of Tokyo. Concanavalin A-sepharose and a-methylmannoside were purchased from PHARMACIA™ and from WAKO™ of Tokyo, respectively. Sephadex-G50 was purchased from PHARMACIA™. M13mp19 was used as a vector for CDNA construction.

The modified nucleotide sequences were made in two steps.

First, a synthetic double-stranded DNA was constructed that codes for human cystatin C, modified to have a glycosylation site at residue number 79. This DNA was made by chemically synthesizing four oligonucleotides using an automated oligonucleotide synthesizer (SEQ ID NO: 25, SEQ ID NO: 26, SEQ ID NO: 27 and SEQ ID NO: 28). The oligonucleotides were chosen on the basis of the known nucleotide sequence of the native human cystatin C gene and the known codon usage of *P. pastoris* (Table 1).

DNA was sequenced using the Sanger method (26, chapter 13). Polypeptides were sequenced using the Edman degradation method in a gas-phase protein automated sequencer (SHIMADZU™ model PSQ2).

TABLE I

| Amino acid | Codon usage |
| --- | --- |
| Glycine | GGT or GGA |
| Glutamic acid | GAG of GAA |
| Aspartic acid | GAC or GAT |
| Valine | GTT or GTC |
| Alanine | GCT or GCC |
| Arginine | AGA or CGT |
| Serine | TCT or TCC |
| Lysine | AAG |
| Asparagine | AAC |
| Methionine | ATG |
| Isoleucine | ATT or ATC |
| Threonine | ACT or ACC |
| Tryptophan | TGG |
| Cysteine | TGT |
| Tyrosine | TAC |
| Leucine | TTG or CTG |
| Phenylalanine | TTC |
| Glutamine | CAA or CAG |
| Histidine | CAC or CAT |
| Proline | CCA or CCT |

The complementary pairs of the four oligonucleotides were annealed together and the resulting double-stranded fragments were ligated using T4 ligase. The resulting synthetic open reading frame contained an XhoI site at the 5' end and an Xba site at the 3' end that were used for cloning. The gene product was ligated into pUC19 (26, chapter 1) and sequenced in both directions to check that the sequence was as predicted.

Second, an N-glycosylation site was introduced at either residue 35 or 36 using the QUICKCHANGE™ site-directed mutagenesis kit (STRATAGENE™, CA) according to manufacturers instructions and using the forward and reverse primers shown in SEQ ID NOs: 29–32.

EXAMPLE 2

Transformation and Clone Selection for Production of Modified Human Cystatin C The yeast expression plasmids pYG-100 (20) and pPICZ α-C containing *Saccharomyces cerevissiae* α factor secretion signal and alcohol oxidase (AOX1) gene promoter were used to express the proteins of the invention. *P. pastoris* strain KM71 was transformed using the Pichia EASY-COM™ transformation system (INVITROGEN™, CA). Zeocin-resistant transformants were selected from yeast extract peptone dextrose sorbitol medium (YPDS) agar plates containing the zeocin. PCR sequencing was used to confirm insertion of the cystatin C gene in Pichia clones.

EXAMPLE 3

Expression and Purification of Modified Human Cystatin C

The Pichia transformants were incubated in yeast minimal medium (YMM). The Pichia transformants were grown at 30° C. for one day in 5 mL of YMM, and then subcultured at 30° C. for four days in 500 mnl of fresh YMM. 100% methanol was added into the fresh YMM to a final concentration of 0.5% methanol every 24 hours to maintain induction of the cystatin gene.

Recombinant modified human cystatin C was secreted in the Pichia culture media. The extracellular proteins were collected using an ultrafiltration system with 10,000 MW cut-off (PELLICON™ cassette filter, MILLIPORE™, Bedford, Mass.). The crude proteins thus recovered were applied to a column of Q-SEPHAROSE FAST FLOW™ (PHARMACIA™, Upsala, Sweden) equilibrated with a linear gradient of 0–0.5 M NaCl in 20 mM Tris-HCI buffer (pH7.5). The fraction including the cystatin was determined by the inhibitory activity against papain as described below. The fraction was applied to a column of sephacryl S-100 HR (PHARMACIA™) equilibrated with 0.15 M NaCl-20 mM Tris-HCI buffer (pH7.5). The fraction which showed the inhibitory activity was collected.

EXAMPLE 4

Assay of Inhibitory Activity and Heat Resistance of Modified Human Cysain C

Cystatin activity was assayed by measuring papain inhibitory activity using Nα-Benzoyl-DL-Arg-p-Nitroanilide (Bz—Arg—NA) (34). 0.1 ml of cystatin sample and 0.1 ml of papain solution (0.5 mg/ml) were pipetted into 0.1 mL of 50 mM Tris-HCI buffer (pH7.5) containing 100 mM Bz—Arg—NA, 2 mM EDTA, and 5 mM cystein. The solution was incubated for 25 min at 37° C. The reaction was stopped with 0.2 ml of 30% acetic acid, and the nitroaniline liberated by enzymatic activity is quantified by measurement of light absorption of the solution at 410nm. The inhibitory activity was expressed as the amount of enzyme (mg) inhibited by 1 mg of inhibitor (U/mg).

Heat resistance assays were performed by heating a solution containing a known amount of cystatin to a controlled temperature for a controlled time; cooling the solution; mixing the cooled cystatin solution with a known amount of papain and protein substrate, and measuring turbidity of the mixture. The recombinant cystatins were heated to 95° C. at a rate of 1° C./min for 30° C. in 50 mM sodium phosphate buffer (pH 7.5). Protein concentration was 1 mg/ml.

At preset temperatures, each heated sample was transferred into a cuvette and the turbidity measured at 500 nm. The residual papain-inhibiting activity of the heated samples was also measured as described above. This procedure was repeated in triplicate.

The above examples are provided by way of illustration only and are in no way intended to limit the scope of the invention. One of skill in the art will see that the invention may be modified in various ways without departing from the spirit or principle of the invention. We claim all such modifications.

References

1. Keppler et al., (1993) In *Proteases and Cancer Colloquium* Queen's Univ., Belfast, 22, 43–49
2. Kuopio et al., (1998) *Cancer Research* 58 (3), 432–436
3. Seymour et al., (1994) *Journal of Agricultural and Food Chemistry* 42, 2421
4. Weerasinghe et al., (1996) *J. Agric. Food Chem.* 44, 2584–2590
5. Izquierdo-Pulido et al., (1994) *J. Agric Food Chem* 42, 616–622
6. Yamashita et al., (1991) *Nippon Suisan Gakkaishi* 57 (10), 1917–1922
7. Barrett et al., *The Biochemical Journal* (1986) Letters 236 (1), 311–312
8. Turk et al., (1991) *FEBS* 285 (2) 213–219
9. Collins et al., (1998) *Oral Microbiol Immunol.* 13 (1), 59–61
10. Barrett (1987) *TIBS* 12, 193–196
11. Grubb et al., (1995) U.S. Pat. No. 5,432,264
12. Korant et al., (1985) *Biochem. and Biophys. Res. Comm.* 127 (3), 1072–1076
13. Abrahamson et al., (1988) *FEBS Letters* 236 (1), 14–18
14. Nakamura et al., (1993) *J. of Biol. Chem.* 268 (17), 12706–12712
15. Saitoh et al., (1998) *Arch Biochem Biophys* 352 (2), 199–206
16. Atkinson et al., (1996) PCT Patent No. WO 96/116173
17. An et al., (1994) *Journal of Food Science* 59 (2), 277
18. Morrissey et al., (1993) *Journal of Food Science* 58 (5), 1050
19. An et al., (1994) *Journal of Food Science* 59 (5), 1013
20. Turk et al., (1990) U.S. Pat. No. 4,902,509
12. Yamashita et al., (1990) *Nippon Suisan Gakkashi* 56 (8) 1271–1277
22. Saeki et al., (1995) *Journal of Food Science* 60 (5),
23. Yamashita et al., (1991) *Comp. Biochem. Physiol.* 100A (3) 749–751
24. Nakamura et al., (1993) *FEBS* 328 (3) 259–262
25. Ausubel et al., (1987). *Current Protocols in Molecular Biology*, ed. Greene Publishing and Wiley-Interscience: New York (with periodic updates)
26. Sarnbrook et al., (1989). *Molecular Cloning: A Laboratory Manual,* 2nd ed., vol. 1–3, ed. Cold Spring Harbor Laboratory Press: Cold Spring Harbor, N.Y.
27. Innis et al., (1990). PCR Protocols: *A Guide to Methods and Applications*, Academic Press: San Diego
28. Nakamura et al., (1996) *FEBS Letters* 383 251–254
29. An et al., (1995) *J. Agric. Food Chem.* 43 327–330
30. Bjorck et al., J. Virol. 64 (2) 941–943
31. Wyatt, R. G. et al., (1980) *Science,* 207, 189–191
32. Betts et al., (1992) *Can. J. Microb.* 38 852–857
33. Invitrogen Product Catalogue, 1998. Invitrogen, Carlsbad, Calif.
34. Barrett et al., (1981) Methods. Enzymol. 80: 771–778

What is claimed:

1. A modified human cystatin C comprising at least one modification of native human cystatin C (SEQ ID NO:2) selected from the group consisting of: Lys (36) Asn, Ala (37) Ser, Ala (37) Thr, Asp (81) Ser, and Asp (81) Thr.

2. The modified human cystatin C of claim 1, wherein said at least one modification increases the heat stability of the modified human cystatin C.

3. The modified human cystatin C of claim 1, wherein said at least one modification is Ala (37) Ser or Ala (37) Thr, and Asp (81) Ser or Asp (81) Thr.

4. The modified human cystatin C of claim 1, said at least one modification is Ala (37) Ser or Asp (81) Thr.

* * * * *

UNITED STATES PATENT AND TRADEMARK OFFICE
CERTIFICATE OF CORRECTION

PATENT NO. : 6,534,477 B2
DATED : March 18, 2003
INVENTOR(S) : Nakai et al.

It is certified that error appears in the above-identified patent and that said Letters Patent is hereby corrected as shown below:

Column 13,
Line 30, "CDNA" should be -- cDNA --.
Line 50, "a-methylmannoside" should be -- α-methylmannoside --.

Column 15,
Line 8, "500 mnl" should be -- 500 ml --.
Line 30, "Cysain C" should be -- Cystatin C --.

Column 16,
Line 33, "WO 96/116173" should be -- WO 96/16173 --.

Signed and Sealed this

Sixteenth Day of December, 2003

JAMES E. ROGAN
*Director of the United States Patent and Trademark Office*

SEQUENCE LISTING

<160> NUMBER OF SEQ ID NOS: 32

<210> SEQ ID NO 1
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 1

```
tcc agt ccc ggc aag ccg ccg cgc ctg gtg gga ggc ccc atg gac gcc      48
Ser Ser Pro Gly Lys Pro Pro Arg Leu Val Gly Gly Pro Met Asp Ala
 1               5                  10                  15 agc gtg gag gag gag ggt gtg cgg cgt gca ctg gac ttt gcc gtc ggc      96
Ser Val Glu Glu Glu Gly Val Arg Arg Ala Leu Asp Phe Ala Val Gly
             20                  25                  30 gag tac aac aaa gcc agc aac gac atg tac cac agc cgc gcg ctg cag     144
Glu Tyr Asn Lys Ala Ser Asn Asp Met Tyr His Ser Arg Ala Leu Gln
         35                  40                  45 gtg gtg cgc gcc cgc aag cag atc gta gct ggg gtg aac tac ttc ttg     192
Val Val Arg Ala Arg Lys Gln Ile Val Ala Gly Val Asn Tyr Phe Leu
     50                  55                  60 gac gtg gag ctg ggc cga acc acg tgt acc aag acc cag ccc aac ttg     240
Asp Val Glu Leu Gly Arg Thr Thr Cys Thr Lys Thr Gln Pro Asn Leu
 65                  70                  75                  80 gac aac tgc ccc ttc cat gac cag cca cat ctg aaa agg aaa gca ttc     288
Asp Asn Cys Pro Phe His Asp Gln Pro His Leu Lys Arg Lys Ala Phe
                 85                  90                  95 tgc tct ttc cag atc tac gct gtg cct tgg cag ggc aca atg acc ttg     336
Cys Ser Phe Gln Ile Tyr Ala Val Pro Trp Gln Gly Thr Met Thr Leu
            100                 105                 110 tcg aaa tcc acc tgt cag gac gcc tag                                  363
Ser Lys Ser Thr Cys Gln Asp Ala
            115                 120
```

<210> SEQ ID NO 2
<211> LENGTH: 120
<212> TYPE: PRT
<213> ORGANISM: Homo sapiens

<400> SEQUENCE: 2

```
Ser Ser Pro Gly Lys Pro Pro Arg Leu Val Gly Gly Pro Met Asp Ala
 1               5                  10                  15

Ser Val Glu Glu Glu Gly Val Arg Arg Ala Leu Asp Phe Ala Val Gly
             20                  25                  30

Glu Tyr Asn Lys Ala Ser Asn Asp Met Tyr His Ser Arg Ala Leu Gln
         35                  40                  45

Val Val Arg Ala Arg Lys Gln Ile Val Ala Gly Val Asn Tyr Phe Leu
     50                  55                  60

Asp Val Glu Leu Gly Arg Thr Thr Cys Thr Lys Thr Gln Pro Asn Leu
 65                  70                  75                  80

Asp Asn Cys Pro Phe His Asp Gln Pro His Leu Lys Arg Lys Ala Phe
                 85                  90                  95

Cys Ser Phe Gln Ile Tyr Ala Val Pro Trp Gln Gly Thr Met Thr Leu
            100                 105                 110

Ser Lys Ser Thr Cys Gln Asp Ala
            115                 120
```

```
<210> SEQ ID NO 3
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 3 tcg agc tcc aag gag gag aat agg ata atc cca ggt ggc atc tat gat      48
Ser Ser Ser Lys Glu Glu Asn Arg Ile Ile Pro Gly Gly Ile Tyr Asp
 1               5                  10                  15 gca gac ctc aat gat gag tgg gta cag cgt gcc ctt cac ttc gcc atc      96
Ala Asp Leu Asn Asp Glu Trp Val Gln Arg Ala Leu His Phe Ala Ile
             20                  25                  30 agc gag tac aac aag gcc acc gaa gat gag tac tac aga cgc ccg ctg     144
Ser Glu Tyr Asn Lys Ala Thr Glu Asp Glu Tyr Tyr Arg Arg Pro Leu
         35                  40                  45 cag gtg ctg cga gcc agg gag cag acc ttt ggg ggt gtg aat tac ttc     192
Gln Val Leu Arg Ala Arg Glu Gln Thr Phe Gly Gly Val Asn Tyr Phe
     50                  55                  60 ttc gac gta gag gtg ggc cgc acc ata tgt acc aag tcc cag ccc aac     240
Phe Asp Val Glu Val Gly Arg Thr Ile Cys Thr Lys Ser Gln Pro Asn
 65                  70                  75                  80 ttg gac acc tgt gcc ttc cat gaa cag cca gaa ctg cag aag aaa cag     288
Leu Asp Thr Cys Ala Phe His Glu Gln Pro Glu Leu Gln Lys Lys Gln
                 85                  90                  95 tta tgc tct ttc gag atc tac gaa gtt ccc tgg gag gac aga atg tcc     336
Leu Cys Ser Phe Glu Ile Tyr Glu Val Pro Trp Glu Asp Arg Met Ser
            100                 105                 110 ctg gtg aat tcc agg tgt caa gaa gcc tag                             366
Leu Val Asn Ser Arg Cys Gln Glu Ala
        115                 120

<210> SEQ ID NO 4
<211> LENGTH: 121
<212> TYPE: PRT
<213> ORGANISM: Homo sapiens

<400> SEQUENCE: 4

Ser Ser Ser Lys Glu Glu Asn Arg Ile Ile Pro Gly Gly Ile Tyr Asp
 1               5                  10                  15

Ala Asp Leu Asn Asp Glu Trp Val Gln Arg Ala Leu His Phe Ala Ile
             20                  25                  30

Ser Glu Tyr Asn Lys Ala Thr Glu Asp Glu Tyr Tyr Arg Arg Pro Leu
         35                  40                  45

Gln Val Leu Arg Ala Arg Glu Gln Thr Phe Gly Gly Val Asn Tyr Phe
     50                  55                  60

Phe Asp Val Glu Val Gly Arg Thr Ile Cys Thr Lys Ser Gln Pro Asn
 65                  70                  75                  80

Leu Asp Thr Cys Ala Phe His Glu Gln Pro Glu Leu Gln Lys Lys Gln
                 85                  90                  95

Leu Cys Ser Phe Glu Ile Tyr Glu Val Pro Trp Glu Asp Arg Met Ser
            100                 105                 110

Leu Val Asn Ser Arg Cys Gln Glu Ala
        115                 120

<210> SEQ ID NO 5
<211> LENGTH: 366
<212> TYPE: DNA
```

<213> ORGANISM: Homo sapiens
<220> FEATURE:
<221> NAME/KEY: CDS
<222> LOCATION: (1)..(366)

<400> SEQUENCE: 5

| tgg | agc | ccc | aag | gag | gag | gat | agg | ata | atc | ccg | ggt | ggc | atc | tat | aac | 48 |
| Trp | Ser | Pro | Lys | Glu | Glu | Asp | Arg | Ile | Ile | Pro | Gly | Gly | Ile | Tyr | Asn | |
| 1 | | | | 5 | | | | | 10 | | | | | 15 | | |

| gca | gac | ctc | aat | gat | gag | tgg | gta | cag | cgt | gcc | ctt | cac | ttc | gcc | atc | 96 |
| Ala | Asp | Leu | Asn | Asp | Glu | Trp | Val | Gln | Arg | Ala | Leu | His | Phe | Ala | Ile | |
| | | | 20 | | | | | 25 | | | | | 30 | | | |

| agc | gag | tat | aac | aag | gcc | acc | aaa | gat | gac | tac | tac | aga | cgt | ccg | ctg | 144 |
| Ser | Glu | Tyr | Asn | Lys | Ala | Thr | Lys | Asp | Asp | Tyr | Tyr | Arg | Arg | Pro | Leu | |
| | 35 | | | | | 40 | | | | | 45 | | | | | |

| cgg | gta | cta | aga | gcc | agg | caa | cag | acc | gtt | ggg | ggg | gtg | aat | tac | ttc | 192 |
| Arg | Val | Leu | Arg | Ala | Arg | Gln | Gln | Thr | Val | Gly | Gly | Val | Asn | Tyr | Phe | |
| 50 | | | | | 55 | | | | | 60 | | | | | | |

| ttc | gac | gta | gag | gtg | ggc | cga | acc | ata | tgt | acc | aag | tcc | cag | ccc | aac | 240 |
| Phe | Asp | Val | Glu | Val | Gly | Arg | Thr | Ile | Cys | Thr | Lys | Ser | Gln | Pro | Asn | |
| 65 | | | | 70 | | | | | 75 | | | | | 80 | | |

| ttg | gac | acc | tgt | gcc | ttc | cat | gaa | cag | cca | gaa | ctg | cag | aag | aaa | cag | 288 |
| Leu | Asp | Thr | Cys | Ala | Phe | His | Glu | Gln | Pro | Glu | Leu | Gln | Lys | Lys | Gln | |
| | | | | 85 | | | | | 90 | | | | | 95 | | |

| ttg | tgc | tct | ttc | gag | atc | tac | gaa | gtt | ccc | tgg | gag | aac | aga | agg | tcc | 336 |
| Leu | Cys | Ser | Phe | Glu | Ile | Tyr | Glu | Val | Pro | Trp | Glu | Asn | Arg | Arg | Ser | |
| | | | 100 | | | | | 105 | | | | | 110 | | | |

| ctg | gtg | aaa | tcc | agg | tgt | caa | gaa | tcc | tag | | | | | | | 366 |
| Leu | Val | Lys | Ser | Arg | Cys | Gln | Glu | Ser | | | | | | | | |
| | 115 | | | | | 120 | | | | | | | | | | |

<210> SEQ ID NO 6
<211> LENGTH: 121
<212> TYPE: PRT
<213> ORGANISM: Homo sapiens

<400> SEQUENCE: 6

Trp Ser Pro Lys Glu Glu Asp Arg Ile Ile Pro Gly Gly Ile Tyr Asn
 1               5                  10                  15

Ala Asp Leu Asn Asp Glu Trp Val Gln Arg Ala Leu His Phe Ala Ile
            20                  25                  30

Ser Glu Tyr Asn Lys Ala Thr Lys Asp Asp Tyr Tyr Arg Arg Pro Leu
        35                  40                  45

Arg Val Leu Arg Ala Arg Gln Gln Thr Val Gly Gly Val Asn Tyr Phe
    50                  55                  60

Phe Asp Val Glu Val Gly Arg Thr Ile Cys Thr Lys Ser Gln Pro Asn
65                  70                  75                  80

Leu Asp Thr Cys Ala Phe His Glu Gln Pro Glu Leu Gln Lys Lys Gln
                85                  90                  95

Leu Cys Ser Phe Glu Ile Tyr Glu Val Pro Trp Glu Asn Arg Arg Ser
            100                 105                 110

Leu Val Lys Ser Arg Cys Gln Glu Ser
        115                 120

<210> SEQ ID NO 7
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 7

```
tgg agc ccc cag gag gag gac agg ata atc gag ggt ggc atc tat gat     48
Trp Ser Pro Gln Glu Glu Asp Arg Ile Ile Glu Gly Gly Ile Tyr Asp
 1               5                  10                  15 gca gac ctc aat gat gag cgg gta cag cgt gcc ctt cac ttt gtc atc     96
Ala Asp Leu Asn Asp Glu Arg Val Gln Arg Ala Leu His Phe Val Ile
            20                  25                  30 agc gag tat aac aag gcc act gaa gat gag tac tac aga cgc ctg ctg    144
Ser Glu Tyr Asn Lys Ala Thr Glu Asp Glu Tyr Tyr Arg Arg Leu Leu
        35                  40                  45 cgg gtg cta cga gcc agg gag cag atc gtg ggc ggg gtg aat tac ttc    192
Arg Val Leu Arg Ala Arg Glu Gln Ile Val Gly Gly Val Asn Tyr Phe
    50                  55                  60 ttc gac ata gag gtg ggc cga acc ata tgt acc aag tcc cag ccc aac    240
Phe Asp Ile Glu Val Gly Arg Thr Ile Cys Thr Lys Ser Gln Pro Asn
65                  70                  75                  80 ttg gac acc tgt gcc ttc cat gaa cag cca gaa ctg cag aag aaa cag    288
Leu Asp Thr Cys Ala Phe His Glu Gln Pro Glu Leu Gln Lys Lys Gln
                85                  90                  95 ttg tgc tct ttc cag atc tac gaa gtt ccc tgg gag gac aga atg tcc    336
Leu Cys Ser Phe Gln Ile Tyr Glu Val Pro Trp Glu Asp Arg Met Ser
            100                 105                 110 ctg gtg aat tcc agg tgt caa gaa gcc tag                            366
Leu Val Asn Ser Arg Cys Gln Glu Ala
        115                 120
```

<210> SEQ ID NO 8
<211> LENGTH: 121
<212> TYPE: PRT
<213> ORGANISM: Homo sapiens

<400> SEQUENCE: 8

```
Trp Ser Pro Gln Glu Glu Asp Arg Ile Ile Glu Gly Gly Ile Tyr Asp
 1               5                  10                  15

Ala Asp Leu Asn Asp Glu Arg Val Gln Arg Ala Leu His Phe Val Ile
            20                  25                  30

Ser Glu Tyr Asn Lys Ala Thr Glu Asp Glu Tyr Tyr Arg Arg Leu Leu
        35                  40                  45

Arg Val Leu Arg Ala Arg Glu Gln Ile Val Gly Gly Val Asn Tyr Phe
    50                  55                  60

Phe Asp Ile Glu Val Gly Arg Thr Ile Cys Thr Lys Ser Gln Pro Asn
65                  70                  75                  80

Leu Asp Thr Cys Ala Phe His Glu Gln Pro Glu Leu Gln Lys Lys Gln
                85                  90                  95

Leu Cys Ser Phe Gln Ile Tyr Glu Val Pro Trp Glu Asp Arg Met Ser
            100                 105                 110

Leu Val Asn Ser Arg Cys Gln Glu Ala
        115                 120
```

<210> SEQ ID NO 9
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 9

```
ggg agt gcc tcg gcc caa tct agg acc ttg gca ggt ggc atc cat gcc     48
```

```
Gly Ser Ala Ser Ala Gln Ser Arg Thr Leu Ala Gly Gly Ile His Ala
 1               5                  10                  15 aca gac ctc aat gac aag agt gtg cag cgt gcc ctg gac ttt gcc atc       96
Thr Asp Leu Asn Asp Lys Ser Val Gln Arg Ala Leu Asp Phe Ala Ile
             20                  25                  30 agc gag tac aac aag gtc att aat aag gat gag tac tac agc cgc cct      144
Ser Glu Tyr Asn Lys Val Ile Asn Lys Asp Glu Tyr Tyr Ser Arg Pro
         35                  40                  45 ctg cag gtg atg gct gcc tac cag cag atc gtg ggt ggg gtg aac tac      192
Leu Gln Val Met Ala Ala Tyr Gln Gln Ile Val Gly Gly Val Asn Tyr
     50                  55                  60 tac ttc aat gtg aag ttc ggt cga acc aca tgc acc aag tcc cag ccc      240
Tyr Phe Asn Val Lys Phe Gly Arg Thr Thr Cys Thr Lys Ser Gln Pro
 65                  70                  75                  80 aac ttg gac aac tgt ccc ttc aat gac cag cca aaa ctg aaa gag gaa      288
Asn Leu Asp Asn Cys Pro Phe Asn Asp Gln Pro Lys Leu Lys Glu Glu
                 85                  90                  95 gag ttc tgc tct ttc cag atc aat gaa gtt ccc tgg gag gat aaa att      336
Glu Phe Cys Ser Phe Gln Ile Asn Glu Val Pro Trp Glu Asp Lys Ile
             100                 105                 110 tcc att ctg aac tac aag tgc cgg aaa gtc tag                          369
Ser Ile Leu Asn Tyr Lys Cys Arg Lys Val
         115                 120
```

<210> SEQ ID NO 10
<211> LENGTH: 122
<212> TYPE: PRT
<213> ORGANISM: Homo sapiens

<400> SEQUENCE: 10

```
Gly Ser Ala Ser Ala Gln Ser Arg Thr Leu Ala Gly Gly Ile His Ala
 1               5                  10                  15

Thr Asp Leu Asn Asp Lys Ser Val Gln Arg Ala Leu Asp Phe Ala Ile
             20                  25                  30

Ser Glu Tyr Asn Lys Val Ile Asn Lys Asp Glu Tyr Tyr Ser Arg Pro
         35                  40                  45

Leu Gln Val Met Ala Ala Tyr Gln Gln Ile Val Gly Gly Val Asn Tyr
     50                  55                  60

Tyr Phe Asn Val Lys Phe Gly Arg Thr Thr Cys Thr Lys Ser Gln Pro
 65                  70                  75                  80

Asn Leu Asp Asn Cys Pro Phe Asn Asp Gln Pro Lys Leu Lys Glu Glu
                 85                  90                  95

Glu Phe Cys Ser Phe Gln Ile Asn Glu Val Pro Trp Glu Asp Lys Ile
             100                 105                 110

Ser Ile Leu Asn Tyr Lys Cys Arg Lys Val
         115                 120
```

<210> SEQ ID NO 11
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 11

```
ctg cca cgc gat gcc cgg gcc cgg ccg cag gag cgc atg gtc gga gaa       48
Leu Pro Arg Asp Ala Arg Ala Arg Pro Gln Glu Arg Met Val Gly Glu
 1               5                  10                  15 ctc cgg gac ctg tcg ccc gac gac ccg cag gtg cag aag gcg gcg cag       96
```

```
Leu Arg Asp Leu Ser Pro Asp Asp Pro Gln Val Gln Lys Ala Ala Gln
             20                  25                  30 gcg gcc gtg gcc agc tac aac atg ggc agc aac agc atc tac tac ttc      144
Ala Ala Val Ala Ser Tyr Asn Met Gly Ser Asn Ser Ile Tyr Tyr Phe
         35                  40                  45 cga gac acg cac atc atc aag gcg cag agc cag ctg gtg gcc ggc atc      192
Arg Asp Thr His Ile Ile Lys Ala Gln Ser Gln Leu Val Ala Gly Ile
 50                  55                  60 aag tac ttc ctg acg atg gag atg ggg agc aca gac tgc cgc aag acc      240
Lys Tyr Phe Leu Thr Met Glu Met Gly Ser Thr Asp Cys Arg Lys Thr
 65                  70                  75                  80 agg gtc act gga gac cac gtc gac ctc acc act tgc ccc ctg gca gca      288
Arg Val Thr Gly Asp His Val Asp Leu Thr Thr Cys Pro Leu Ala Ala
                 85                  90                  95 ggg gcg cag cag gag aag ctg cgc tgt gac ttt gag gtc ctt gtg gtt      336
Gly Ala Gln Gln Glu Lys Leu Arg Cys Asp Phe Glu Val Leu Val Val
            100                 105                 110 ccc tgg cag aac tcc tct cag ctc cta aag cac aac tgt gtg cag atg      384
Pro Trp Gln Asn Ser Ser Gln Leu Leu Lys His Asn Cys Val Gln Met
        115                 120                 125 tga                                                                   387

<210> SEQ ID NO 12
<211> LENGTH: 128
<212> TYPE: PRT
<213> ORGANISM: Homo sapiens

<400> SEQUENCE: 12

Leu Pro Arg Asp Ala Arg Ala Arg Pro Gln Glu Arg Met Val Gly Glu
 1               5                  10                  15

Leu Arg Asp Leu Ser Pro Asp Asp Pro Gln Val Gln Lys Ala Ala Gln
             20                  25                  30

Ala Ala Val Ala Ser Tyr Asn Met Gly Ser Asn Ser Ile Tyr Tyr Phe
         35                  40                  45

Arg Asp Thr His Ile Ile Lys Ala Gln Ser Gln Leu Val Ala Gly Ile
 50                  55                  60

Lys Tyr Phe Leu Thr Met Glu Met Gly Ser Thr Asp Cys Arg Lys Thr
 65                  70                  75                  80

Arg Val Thr Gly Asp His Val Asp Leu Thr Thr Cys Pro Leu Ala Ala
                 85                  90                  95

Gly Ala Gln Gln Glu Lys Leu Arg Cys Asp Phe Glu Val Leu Val Val
            100                 105                 110

Pro Trp Gln Asn Ser Ser Gln Leu Leu Lys His Asn Cys Val Gln Met
        115                 120                 125

<210> SEQ ID NO 13
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 13 cgg ccg cag gag cgc atg gtc gga gaa ctc cgg gac ctg tcg ccc gac       48
Arg Pro Gln Glu Arg Met Val Gly Glu Leu Arg Asp Leu Ser Pro Asp
 1               5                  10                  15 gac ccg cag gtg cag aag gcg gcg cag gcg gcc gtg gcc agc tac aac       96
Asp Pro Gln Val Gln Lys Ala Ala Gln Ala Ala Val Ala Ser Tyr Asn
             20                  25                  30
```

```
atg ggc agc aac agc atc tac tac ttc cga gac acg cac atc atc aag    144
Met Gly Ser Asn Ser Ile Tyr Tyr Phe Arg Asp Thr His Ile Ile Lys
            35                  40                  45 gcg cag agc cag ctg gtg gcc ggc atc aag tac ttc ctg acg atg gag    192
Ala Gln Ser Gln Leu Val Ala Gly Ile Lys Tyr Phe Leu Thr Met Glu
 50                  55                  60 atg ggg agc aca gac tgc cgc aag acc agg gtc act gga gac cac gtc    240
Met Gly Ser Thr Asp Cys Arg Lys Thr Arg Val Thr Gly Asp His Val
 65                  70                  75                  80 gac ctc acc act tgc ccc ctg gca gca ggg gcg cag cag gag aag ctg    288
Asp Leu Thr Thr Cys Pro Leu Ala Ala Gly Ala Gln Gln Glu Lys Leu
                 85                  90                  95 cgc tgt gac ttt gag gtc ctt gtg gtt ccc tgg cag aac tcc tct cag    336
Arg Cys Asp Phe Glu Val Leu Val Val Pro Trp Gln Asn Ser Ser Gln
            100                 105                 110 ctc cta aag cac aac tgt gtg cag atg tga                            366
Leu Leu Lys His Asn Cys Val Gln Met
            115                 120

<210> SEQ ID NO 14
<211> LENGTH: 121
<212> TYPE: PRT
<213> ORGANISM: Homo sapiens

<400> SEQUENCE: 14

Arg Pro Gln Glu Arg Met Val Gly Glu Leu Arg Asp Leu Ser Pro Asp
  1               5                  10                  15

Asp Pro Gln Val Gln Lys Ala Ala Gln Ala Ala Val Ala Ser Tyr Asn
                 20                  25                  30

Met Gly Ser Asn Ser Ile Tyr Tyr Phe Arg Asp Thr His Ile Ile Lys
            35                  40                  45

Ala Gln Ser Gln Leu Val Ala Gly Ile Lys Tyr Phe Leu Thr Met Glu
 50                  55                  60

Met Gly Ser Thr Asp Cys Arg Lys Thr Arg Val Thr Gly Asp His Val
 65                  70                  75                  80

Asp Leu Thr Thr Cys Pro Leu Ala Ala Gly Ala Gln Gln Glu Lys Leu
                 85                  90                  95

Arg Cys Asp Phe Glu Val Leu Val Val Pro Trp Gln Asn Ser Ser Gln
            100                 105                 110

Leu Leu Lys His Asn Cys Val Gln Met
            115                 120

<210> SEQ ID NO 15
<211> LENGTH: 351
<212> TYPE: DNA
<213> ORGANISM: Gallus sp.
<220> FEATURE:
<221> NAME/KEY: CDS
<222> LOCATION: (1)..(351)

<400> SEQUENCE: 15 agc gag gac cgc tcc cgg ctc ctg ggg gct cca gtg cct gta gat gag    48
Ser Glu Asp Arg Ser Arg Leu Leu Gly Ala Pro Val Pro Val Asp Glu
  1               5                  10                  15 aac gac gag ggc ttg caa cgg gcc ctg cag ttc gcg atg gcc gag tac    96
Asn Asp Glu Gly Leu Gln Arg Ala Leu Gln Phe Ala Met Ala Glu Tyr
                 20                  25                  30 aac agg gcc agc aac gat aag tac tcc agc cgg gtg gtg cgg gtc atc    144
Asn Arg Ala Ser Asn Asp Lys Tyr Ser Ser Arg Val Val Arg Val Ile
            35                  40                  45
```

```
agc gcc aag cgg cag ctc gtg tct gga atc aag tac atc ctg cag gtt      192
Ser Ala Lys Arg Gln Leu Val Ser Gly Ile Lys Tyr Ile Leu Gln Val
    50                  55                  60 gag att ggt cgc aca act tgc ccc aag tca tca ggt gat ctc cag agc      240
Glu Ile Gly Arg Thr Thr Cys Pro Lys Ser Ser Gly Asp Leu Gln Ser
65                  70                  75                  80 tgc gaa ttc cac gat gag cca gag atg gct aag tat acc aca tgc acc      288
Cys Glu Phe His Asp Glu Pro Glu Met Ala Lys Tyr Thr Thr Cys Thr
                85                  90                  95 ttt gta gtg tac agt att cct tgg cta aac caa att aaa ctg ctg gaa      336
Phe Val Val Tyr Ser Ile Pro Trp Leu Asn Gln Ile Lys Leu Leu Glu
            100                 105                 110 agc aag tgc cag taa                                                  351
Ser Lys Cys Gln
        115
```

<210> SEQ ID NO 16
<211> LENGTH: 116
<212> TYPE: PRT
<213> ORGANISM: Gallus sp.

<400> SEQUENCE: 16

```
Ser Glu Asp Arg Ser Arg Leu Leu Gly Ala Pro Val Pro Val Asp Glu
1               5                   10                  15

Asn Asp Glu Gly Leu Gln Arg Ala Leu Gln Phe Ala Met Ala Glu Tyr
            20                  25                  30

Asn Arg Ala Ser Asn Asp Lys Tyr Ser Ser Arg Val Val Arg Val Ile
        35                  40                  45

Ser Ala Lys Arg Gln Leu Val Ser Gly Ile Lys Tyr Ile Leu Gln Val
    50                  55                  60

Glu Ile Gly Arg Thr Thr Cys Pro Lys Ser Ser Gly Asp Leu Gln Ser
65                  70                  75                  80

Cys Glu Phe His Asp Glu Pro Glu Met Ala Lys Tyr Thr Thr Cys Thr
                85                  90                  95

Phe Val Val Tyr Ser Ile Pro Trp Leu Asn Gln Ile Lys Leu Leu Glu
            100                 105                 110

Ser Lys Cys Gln
        115
```

<210> SEQ ID NO 17
<211> LENGTH: 336
<212> TYPE: DNA
<213> ORGANISM: Cyprinus carpio
<220> FEATURE:
<221> NAME/KEY: CDS
<222> LOCATION: (1)..(336)

<400> SEQUENCE: 17

```
act ggg att cct gga ggc ctt gta gat gca gac att aac gat aaa gat       48
Thr Gly Ile Pro Gly Gly Leu Val Asp Ala Asp Ile Asn Asp Lys Asp
1               5                   10                  15 gtt cag aag gcg tta cgc ttc gca gtg gac cat tac aac ggc caa agc       96
Val Gln Lys Ala Leu Arg Phe Ala Val Asp His Tyr Asn Gly Gln Ser
            20                  25                  30 aac gat gcg ttt gtg cgt aaa gtt tcc aaa gta atc aag gtt caa caa      144
Asn Asp Ala Phe Val Arg Lys Val Ser Lys Val Ile Lys Val Gln Gln
        35                  40                  45 caa gtt gcc gct ggc atg aaa tac atc ttc act gtg aag atg gaa gta      192
Gln Val Ala Ala Gly Met Lys Tyr Ile Phe Thr Val Lys Met Glu Val
    50                  55                  60
```

```
gcc tcc tgc aaa aag ggt gga gtt aag acc atg tgt gcc gtt ccg aag     240
Ala Ser Cys Lys Lys Gly Gly Val Lys Thr Met Cys Ala Val Pro Lys
 65                  70                  75                  80 aat ccc agt att gaa cag gtc att cag tgc aaa ata acg gtc tgg agc     288
Asn Pro Ser Ile Glu Gln Val Ile Gln Cys Lys Ile Thr Val Trp Ser
                 85                  90                  95 cag cca tgg tta aac tcc ttg aaa gtc act gaa aac acc tgc atg tag     336
Gln Pro Trp Leu Asn Ser Leu Lys Val Thr Glu Asn Thr Cys Met
            100                 105                 110
```

<210> SEQ ID NO 18
<211> LENGTH: 111
<212> TYPE: PRT
<213> ORGANISM: Cyprinus carpio

<400> SEQUENCE: 18

```
Thr Gly Ile Pro Gly Gly Leu Val Asp Ala Asp Ile Asn Asp Lys Asp
 1               5                  10                  15

Val Gln Lys Ala Leu Arg Phe Ala Val Asp His Tyr Asn Gly Gln Ser
                20                  25                  30

Asn Asp Ala Phe Val Arg Lys Val Ser Lys Val Ile Lys Val Gln Gln
             35                  40                  45

Gln Val Ala Ala Gly Met Lys Tyr Ile Phe Thr Val Lys Met Glu Val
 50                  55                  60

Ala Ser Cys Lys Lys Gly Gly Val Lys Thr Met Cys Ala Val Pro Lys
 65                  70                  75                  80

Asn Pro Ser Ile Glu Gln Val Ile Gln Cys Lys Ile Thr Val Trp Ser
                 85                  90                  95

Gln Pro Trp Leu Asn Ser Leu Lys Val Thr Glu Asn Thr Cys Met
            100                 105                 110
```

<210> SEQ ID NO 19
<211> LENGTH: 336
<212> TYPE: DNA
<213> ORGANISM: Oncorhynchus keta
<220> FEATURE:
<221> NAME/KEY: CDS
<222> LOCATION: (1)..(336)

<400> SEQUENCE: 19

```
ggt ttg gtc gga ggc ccc atg gac gca aat atg aac gac caa gga acg      48
Gly Leu Val Gly Gly Pro Met Asp Ala Asn Met Asn Asp Gln Gly Thr
 1               5                  10                  15 aga gac gcc ctg cag ttc gcg gtg gtc gaa cac aac aag aaa aca aac      96
Arg Asp Ala Leu Gln Phe Ala Val Val Glu His Asn Lys Lys Thr Asn
                20                  25                  30 gac atg ttt gtc agg cag gtg gcc aag gtt gtc aat gca cag aaa cag     144
Asp Met Phe Val Arg Gln Val Ala Lys Val Val Asn Ala Gln Lys Gln
             35                  40                  45 gtg gta tct ggg atg aag tac atc ttc aca gtg cag atg ggc agg acc     192
Val Val Ser Gly Met Lys Tyr Ile Phe Thr Val Gln Met Gly Arg Thr
 50                  55                  60 cca tgc agg aag gga ggt gtt gag aag atc tgc tcc gtg cac aaa gac     240
Pro Cys Arg Lys Gly Gly Val Glu Lys Ile Cys Ser Val His Lys Asp
 65                  70                  75                  80 ccg cag atg gct gtg ccc tac aag tgc acc ttc gag gtg tgg agc cgc     288
Pro Gln Met Ala Val Pro Tyr Lys Cys Thr Phe Glu Val Trp Ser Arg
                 85                  90                  95 ccc tgg atg agc gat atc cag atg gtc aag aac cag tgt gaa agt taa     336
Pro Trp Met Ser Asp Ile Gln Met Val Lys Asn Gln Cys Glu Ser
            100                 105                 110
```

<210> SEQ ID NO 20
<211> LENGTH: 111
<212> TYPE: PRT
<213> ORGANISM: Oncorhynchus keta

<400> SEQUENCE: 20

```
Gly Leu Val Gly Gly Pro Met Asp Ala Asn Met Asn Asp Gln Gly Thr
 1               5                  10                  15

Arg Asp Ala Leu Gln Phe Ala Val Val Glu His Asn Lys Lys Thr Asn
             20                  25                  30

Asp Met Phe Val Arg Gln Val Ala Lys Val Val Asn Ala Gln Lys Gln
         35                  40                  45

Val Val Ser Gly Met Lys Tyr Ile Phe Thr Val Gln Met Gly Arg Thr
     50                  55                  60

Pro Cys Arg Lys Gly Gly Val Glu Lys Val Cys Ser Val His Lys Asp
 65                  70                  75                  80

Pro Gln Met Ala Val Pro Tyr Lys Cys Thr Phe Glu Val Trp Ser Arg
                 85                  90                  95

Pro Trp Met Ser Asp Ile Gln Met Val Lys Asn Gln Cys Glu Ser
            100                 105                 110
```

<210> SEQ ID NO 21
<211> LENGTH: 336
<212> TYPE: DNA
<213> ORGANISM: Oncorhynchus mykiss
<220> FEATURE:
<221> NAME/KEY: CDS
<222> LOCATION: (1)..(336)

<400> SEQUENCE: 21

```
ggt ttg atc gga ggc ccc atg gac gca aat atg aac gac caa gga acg      48
Gly Leu Ile Gly Gly Pro Met Asp Ala Asn Met Asn Asp Gln Gly Thr
 1               5                  10                  15 aga gac gcc ctg cag ttc gcg gtg gtc gaa cac aac aag aaa aca aac      96
Arg Asp Ala Leu Gln Phe Ala Val Val Glu His Asn Lys Lys Thr Asn
             20                  25                  30 gac atg ttt gtc agg cag gtg gcc aag gtt gtc aat gca cag aag cag     144
Asp Met Phe Val Arg Gln Val Ala Lys Val Val Asn Ala Gln Lys Gln
         35                  40                  45 gtg gta tct ggg atg aag tac atc ttc aca gtg cag atg ggc agg acc     192
Val Val Ser Gly Met Lys Tyr Ile Phe Thr Val Gln Met Gly Arg Thr
     50                  55                  60 cca tgc agg aag gga ggt gtt gag aag gtc tgc tcc gtg cac aag gac     240
Pro Cys Arg Lys Gly Gly Val Glu Lys Val Cys Ser Val His Lys Asp
 65                  70                  75                  80 cca cag atg gct gtg ccc tac aag tgc acc ttc gag gtg tgg agc cgc     288
Pro Gln Met Ala Val Pro Tyr Lys Cys Thr Phe Glu Val Trp Ser Arg
                 85                  90                  95 ccc tgg atg agc gat atc cag atg gtc aag aac cag tgt gaa agt taa     336
Pro Trp Met Ser Asp Ile Gln Met Val Lys Asn Gln Cys Glu Ser
            100                 105                 110
```

<210> SEQ ID NO 22
<211> LENGTH: 111
<212> TYPE: PRT
<213> ORGANISM: Oncorhynchus mykiss

<400> SEQUENCE: 22

Gly Leu Ile Gly Gly Pro Met Asp Ala Asn Met Asn Asp Gln Gly Thr

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |

Arg Asp Ala Leu Gln Phe Ala Val Val Glu His Asn Lys Lys Thr Asn
                20              25          30

Asp Met Phe Val Arg Gln Val Ala Lys Val Val Asn Ala Gln Lys Gln
     35                40              45

Val Val Ser Gly Met Lys Tyr Ile Phe Thr Val Gln Met Gly Arg Thr
 50              55              60

Pro Cys Arg Lys Gly Gly Val Glu Lys Val Cys Ser Val His Lys Asp
65              70              75          80

Pro Gln Met Ala Val Pro Tyr Lys Cys Thr Phe Glu Val Trp Ser Arg
                85              90          95

Pro Trp Met Ser Asp Ile Gln Met Val Lys Asn Gln Cys Glu Ser
     100               105            110

<210> SEQ ID NO 23
<211> LENGTH: 357
<212> TYPE: DNA
<213> ORGANISM: Bos taurus
<220> FEATURE:
<221> NAME/KEY: CDS
<222> LOCATION: (1)..(357)

<400> SEQUENCE: 23

```
cag ggc cct agg aag ggt cgc ctg ctg ggc ggc ctg atg gag gcg gac      48
Gln Gly Pro Arg Lys Gly Arg Leu Leu Gly Gly Leu Met Glu Ala Asp
 1               5                  10                  15 gtc aat gag gag ggc gtg cag gag gcg ctg tcc ttt gcg gtc agc gag      96
Val Asn Glu Glu Gly Val Gln Glu Ala Leu Ser Phe Ala Val Ser Glu
             20                  25                  30 ttc aac aag cgg agc aac gac gct tac cag agc cgc gtg gtg cgc gtg     144
Phe Asn Lys Arg Ser Asn Asp Ala Tyr Gln Ser Arg Val Val Arg Val
         35                  40                  45 gtg cgc gcc cgc aag cag gtc gtg tca ggg atg aac tat ttc ttg gac     192
Val Arg Ala Arg Lys Gln Val Val Ser Gly Met Asn Tyr Phe Leu Asp
     50                  55                  60 gtg gag ctt ggc cgg act aca tgt acc aag tcc cag gcc aac ttt gac     240
Val Glu Leu Gly Arg Thr Thr Cys Thr Lys Ser Gln Ala Asn Phe Asp
 65                  70                  75                  80 agc tgt ccc ttc cat aac cag ccg cac ctg aag agg gaa aag ctg tgc     288
Ser Cys Pro Phe His Asn Gln Pro His Leu Lys Arg Glu Lys Leu Cys
                 85                  90                  95 tcc ttc cag gtt tac gtc gtc cca tgg atg aac acc atc aac ctg gtg     336
Ser Phe Gln Val Tyr Val Val Pro Trp Met Asn Thr Ile Asn Leu Val
            100                 105                 110 aag ttt agc tgc cag gat taa                                          357
Lys Phe Ser Cys Gln Asp
        115
```

<210> SEQ ID NO 24
<211> LENGTH: 118
<212> TYPE: PRT
<213> ORGANISM: Bos taurus

<400> SEQUENCE: 24

Gln Gly Pro Arg Lys Gly Arg Leu Leu Gly Gly Leu Met Glu Ala Asp
 1               5                  10                  15

Val Asn Glu Glu Gly Val Gln Glu Ala Leu Ser Phe Ala Val Ser Glu
             20                  25                  30

Phe Asn Lys Arg Ser Asn Asp Ala Tyr Gln Ser Arg Val Val Arg Val
         35                  40                  45

```
Val Arg Ala Arg Lys Gln Val Val Ser Gly Met Asn Tyr Phe Leu Asp
    50                  55                  60

Val Glu Leu Gly Arg Thr Thr Cys Thr Lys Ser Gln Ala Asn Phe Asp
65                  70                  75                  80

Ser Cys Pro Phe His Asn Gln Pro His Leu Lys Arg Glu Lys Leu Cys
                85                  90                  95

Ser Phe Gln Val Tyr Val Val Pro Trp Met Asn Thr Ile Asn Leu Val
            100                 105                 110

Lys Phe Ser Cys Gln Asp
        115
```

<210> SEQ ID NO 25
<211> LENGTH: 115
<212> TYPE: DNA
<213> ORGANISM: Artificial Sequence
<220> FEATURE:
<223> OTHER INFORMATION: Description of Artificial Sequence: first of
      four oligonucleotides used to create a nucleotide
      coding for modified human cystatin C

<400> SEQUENCE: 25
gtatctctcg agaaaagatc ttctccaggt aagccaccaa gattggtcgg tggtccaatg      60
gacgcctctg tcgaggagga gggtgtcaga agagccttgg acttcgccgt cggtg          115

<210> SEQ ID NO 26
<211> LENGTH: 115
<212> TYPE: DNA
<213> ORGANISM: Artificial Sequence
<220> FEATURE:
<223> OTHER INFORMATION: Description of Artificial Sequence: the second
      of four oligonucleotides used to create a nucleotide
      coding for synthetic human cystatin C

<400> SEQUENCE: 26
caagaagtag ttgacaccgg cgacaatttg ctttctggct ctgacgactt gcaaggctct      60
ggagtggtac atgtcgttag aggccttgtt gtactcaccg acggcgaagt ccaag           115

<210> SEQ ID NO 27
<211> LENGTH: 115
<212> TYPE: DNA
<213> ORGANISM: Artificial Sequence
<220> FEATURE:
<223> OTHER INFORMATION: Description of Artificial Sequence: the third
      of four oligonucleotides used to create a nucleotide
      coding for synthetic human cystatin C

<400> SEQUENCE: 27
caaattgtcg ccggtgtcaa ctacttcttg gacgttgagt tgggtagaac tacttgtact      60
aagactcaac caaacttgac taactgtcca ttccacgacc aaccacactt gaaga           115

<210> SEQ ID NO 28
<211> LENGTH: 115
<212> TYPE: DNA
<213> ORGANISM: Artificial Sequence
<220> FEATURE:
<223> OTHER INFORMATION: Description of Artificial Sequence: the fourth
      of four oligonucleotides used to create a nucleotide
      coding for synthetic human cystatin C

<400> SEQUENCE: 28
tgttctagat caggcgtctt gacaagtaga cttagacaaa gtcatagtac cttgccatgg      60
gacggcgtaa atttggaaag aacagaaggc ctttctcttc aagtgtggtt ggtcg           115

```
<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: forward
      primer used in site-directed mutagenesis to intro. a
      glycosylation site at residue 35 of a modified human cystatin C

<400> SEQUENCE: 29
ggtgagtaca acaagtcctc taacgacatg                                          30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: reverse
      primer used in site-directed mutagenesis to intro. a
      glycosylation site at residue 35 of a modified human cystatin C

<400> SEQUENCE: 30
catgtcgtta gaggacttgt tgtactcacc                                          30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: forward
      primer used in site-directed mutagenesis to intro. a
      glycosylation site at residue 36 of a modified human cystatin C

<400> SEQUENCE: 31
ggtgagtaca acaacgcctc taacgacatg                                          30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: reverse
      primer used in site-directed mutagenesis to intro. a
      glycosylation site at residue 36 of a modified human cystatin C

<400> SEQUENCE: 32
catgtcgtta gaggcgttgt tgtactcacc                                          30
```